US009315772B2

(12) United States Patent
Vannier et al.

(10) Patent No.: US 9,315,772 B2
(45) Date of Patent: Apr. 19, 2016

(54) CROSSLINKED HYALURONAN HYDROGELS FOR 3D CELL CULTURE

(75) Inventors: Jean-Pierre Vannier, Saint Jacques sur Darnetal (FR); Laurent David, Paris (FR); Didier Lecerf, Bose Roger sur Buchy (FR); Virginie Dulong, Rouen (FR); Berenice Coquerel, Notre Dame de Bondeville (FR); Elise Demange, Rouen (FR)

(73) Assignee: UNIVERSITE DE ROUEN, Mont-Saint-Aignan (FR)

( * ) Notice: Subject to any disclaimer, the term of this patent is extended or adjusted under 35 U.S.C. 154(b) by 39 days.

(21) Appl. No.: 13/704,384

(22) PCT Filed: Jun. 22, 2011

(86) PCT No.: PCT/EP2011/060465
§ 371 (c)(1),
(2), (4) Date: Feb. 22, 2013

(87) PCT Pub. No.: WO2011/161172
PCT Pub. Date: Dec. 29, 2011

(65) Prior Publication Data
US 2013/0260464 A1    Oct. 3, 2013

(30) Foreign Application Priority Data

Jun. 22, 2010   (EP) .................................... 10305666
Mar. 24, 2011   (EP) .................................... 11305333

(51) Int. Cl.
C12N 5/00   (2006.01)

(52) U.S. Cl.
CPC ............ *C12N 5/0068* (2013.01); *C12N 5/0062* (2013.01); *C12N 2533/80* (2013.01); *C12N 2537/10* (2013.01)

(58) Field of Classification Search
None
See application file for complete search history.

(56) References Cited

U.S. PATENT DOCUMENTS 3,551,556 A  * 12/1970  Kliment et al. ............... 424/434
5,462,976 A  * 10/1995  Matsuda et al. ............... 522/74
2008/0248570 A1 * 10/2008  Turner et al. .................. 435/377

FOREIGN PATENT DOCUMENTS

WO    WO 2009/026158    2/2009

OTHER PUBLICATIONS

David et al., Acta Biomaterialia 4: 256-263 (2008).*
http://web.archive.org/web/20080325020601/http://en.wikipedia.org/wiki/Oil_bath, archived Mar. 25, 2008, accessed Feb. 10, 2014.*
Cloyd et al., Eur. Spine J. 16: 1892-1898 (2007).*
David, L., et al., "Hyaluronan hydrogel: An appropriate three-dimensional model for evaluation of anticancer drug sensitivity", Acta Biomaterialia 4:2, 256-263, Feb. 9, 2008.
Kim, J., et al., "Bone regeneration using hyaluronic acid-based hydrogel with bone morphogenic protein-2 and human mesenchymal stem cells", Biomaterials, 28:10, 1830-1837, Jan. 23, 2007.
(Continued)

*Primary Examiner* — Patricia A Leith
*Assistant Examiner* — Erin M Bowers
(74) *Attorney, Agent, or Firm* — Frost Brown Todd LLC (57) ABSTRACT

The present invention relates to a new method for treating or processing a cross-linked hyaluronan hydrogel prior to its use in applications involving three-dimensional cell culture. The invention also relates to cross-linked hyaluronan hydrogels prepared by such a method and to their use in 3D cell culture, stem cell/tissue engineering, drug discovery, toxicology testing, and broad cell biology applications.

6 Claims, 6 Drawing Sheets

(56) References Cited

OTHER PUBLICATIONS

Liu, M.D., Y.; et al., "Crosslinked hyaluronan hydrogels containing mitimycin C reduce postoperative abdominal adhesions", Fertility and Sterility, vol. 83, Supp 1, pp. 1275-1283, Apr. 1, 2005.

Shu, XZ, et al., "Attachment and spreading of fibroblasts on an RGD peptide-modified injectable hyaluronan hydrogel", J, Biomed. Mater. Rex. 68:2, 365-375, Feb. 1, 2003.

* cited by examiner

CROSSLINKED HYALURONAN HYDROGELS FOR 3D CELL CULTURE

RELATED PATENT APPLICATIONS

The present application claims priority to European Patent Application No. EP 10 305 666 filed on Jun. 22, 2010 and to European Patent Application No. EP 11 305 333 filed on Mar. 24, 2011. Each of the European Patent Applications is incorporated herein by reference in its entirety.

BACKGROUND OF THE INVENTION

The majority of cell culture studies have been performed on 2-dimensional (2D) surfaces such as micro-well plates, tissue culture flasks, and Petri dishes because of the ease, convenience, and high cell viability of 2D culture. Although these conventional 2D cell culture systems have tremendously improved our understanding of basic cell biology, they have proved to be insufficient and unsuitable for new challenges in cell biology as well as for pharmaceutical assays. Indeed, 2D culture systems fall short of reproducing the complex and dynamic environments of the in vivo situation, which are known to affect cell morphology, growth rates, contact geometries, transport properties, and numerous other cellular functions.

Three-dimensional (3D) cell culture matrices, also called scaffolds, have been introduced to overcome 2D culture limitations. These matrices are porous substrates that can support cell growth, organization, and differentiation on or within their structure. It has been demonstrated that, in comparison to conventional cultures, cells in 3D cultures more closely resemble the in vivo situation with regard to cell shape and cellular environment. Architectural and material diversity is much greater on 3D matrices than on 2D substrates. A variety of fabrication processes and biomaterials have been developed or adapted to produce cellular supports with different physical appearance, porosity, permeability, mechanical characteristics, and nano-scale surface morphology to match the diversity of in vivo environments.

A lot of efforts have focused on exploring the use of natural substances related to the extracellular matrix as biomaterials for scaffolds. Indeed, the behavior of normal and tumor cells is known to be directly conditioned by the composition of the extracellular matrix (ECM) of which hyaluronan and collagens are the principal constituents. Hyaluronan, a glycosaminoglycan composed of a repeating disaccharide of glucuronic acid and N-acetylglycosamine ($\beta 1,4$-GlcUA-$\beta 1$, 3-GlcNAc)$_n$, contributes significantly to cell proliferation and migration, and participates in a number of cell surface receptor interactions. It is generally accepted that hyaluronan is also implicated in tumor progression (Stern, Pathol. Biol., 2005, 53: 372-382). High contents of intracellular hyaluronan and its accumulation in the extracellular matrix create a microenvironment favorable for migration, proliferation and invasiveness of malignant cells (Delpech et al., J. Intern. Med., 1997, 242: 41-48; Toole, J. Biol. Chem., 2002, 277: 4593-4596). Thus, the invasive capability of malignant cells depends on interactions with the extracellular matrix and is promoted by hyaluronan production, as shown, for example, in the case of colon carcinoma (Kim et al., Cancer Res., 2004, 64: 4569-4576), breast adenocarcinoma (Auviven et al., Am. J. Pathol., 2000, 156: 529-536) and gastric cancers (Vizoso et al., Eur. J. Surg. Oncol., 2004, 30: 318-324). The activity of cancer cells is controlled by transductional mechanisms involving hyaluronan membrane receptors such as RHAMM or CD44. In particular, CD44, which is a ubiquitous cell surface adhesion molecule and the main receptor for hyaluronan, is implicated in cell-to-cell and cell-ECM interactions and migration of cancer cell (Assman et al., J. Pathol., 2001, 195: 191-196; Knudson et al., Matrix Biol., 2002, 21: 15-23; Ponta et al., Nat. Rev. Mol. Cell Biol., 2003, 4: 33-45). These observations have led to the use of hyaluronan as biomaterial for 3D matrices.

In particular, a reticulated hyaluronan hydrogel suitable for 3D cell culture has been developed in the laboratory of the present inventors and used to examine cancer cell invasion in 3D and evaluate cancer cell sensitivity to anticancer drugs (David et al., Matrix Biology, 2004, 23: 183-193; David et al., Cell Prolif., 2008, 41: 348-364; David et al., Acta Biomaterialia, 2008, 4: 256-263; Coquerel et al., Glia, 2009, 57: 1716-1726). However, there is always a need in the art for 3D matrices with improved properties.

SUMMARY OF THE INVENTION

The present invention generally relates to a method for preparing a cross-linked hyaluronan hydrogel that can be used in a variety of applications involving three-dimensional cell culture. More specifically, the invention provides a method for treating or processing a cross-linked hyaluronan hydrogel before the hydrogel is used as a scaffold for cell culture. In particular, a method according to the invention yields a hyaluronan hydrogel with improved properties compared to a similar hydrogel that has not been submitted to such processing. Indeed, a hydrogel according to the present invention exhibits greater rehydration properties, which results in a more complete and uniform cell migration into the matrix, and therefore a more satisfactory 3D cell culture.

Accordingly, in one aspect, the present invention provides a method for obtaining a cross-linked hyaluronan hydrogel that is suitable for use in 3D cell culture, said method comprising steps of: (a) lyophilizing the hyaluronan hydrogel to obtain a lyophilized hyaluronan hydrogel or providing a lyophilized hyaluronan hydrogel; and (b) sterilizing the lyophilized hyaluronan hydrogel first by heating the hydrogel and then by immersing the hydrogel in alcohol and submitting the immersed hydrogel to physical compression.

Hyaluronan hydrogels that can be processed according to a method of the present invention may consist essentially in cross-linked hyaluronan; or, alternatively, the hydrogels may comprise cross-linked hyaluronan and at least one of: biomolecules, biologically active agents, pharmaceutically active agents, and combinations thereof. Examples of suitable biomolecules include, but are not limited to, collagens, basal adhesion molecules, proteoglycans or glycosaminoglycan chains, hormones, growth factors, and the like.

In certain embodiments, the heating step in a method of the invention is performed for between 30 minutes and 1 hour using an oil bath at 100° C.

In certain preferred embodiments, after heating, the lyophilized hyaluronan hydrogel is immersed in pure ethanol at room temperature. In certain embodiments, between the heating step and the immersing step, the hydrogel may be left to stand at room temperature under sterile conditions (e.g., in a sterile hood). In other embodiments, the hydrogel is immersed in alcohol immediately after the heating step.

In certain preferred embodiments, the step of submitting the immersed hydrogel to physical compression eliminates any air trapped in the hydrogel.

In certain embodiments, a method of the invention further comprises a step of: prior to sterilization, storing the lyophilized hyaluronon hydrogel at below 0° C. temperature, for example at −20° C.

In certain embodiments, a method of the invention further comprises a step of: prior to sterilization, cutting the lyophilized hyaluronan hydrogel to desired shape and dimensions. Shape and dimensions will generally be dictated by the intended use of the hydrogel.

In certain embodiments, a method of the invention further comprises a step of: following sterilization, storing the sterilized hyaluronan hydrogel at −20° C. under sterile conditions.

In certain embodiments, a method of the invention further comprises a step of: rehydrating the sterilized hydrogel prior to use. Preferably, the step of rehydrating is performed using a rehydrating medium, such as a cell culture medium, and the sterilized hydrogel is swelled to a desired mass or volume. In certain embodiments, the hydrogel is swelled about 100-fold in mass.

In another aspect, the present invention provides a sterilized cross-linked hyaluronan hydrogel which is obtained, or is susceptible to be obtained, according to a method of the present invention. The present invention also provides a rehydrated cross-linked hyaluronan hydrogel which is obtained, or is susceptible to be obtained, according to a method of the present invention.

In certain preferred embodiments of the invention, sterilized cross-linked hyaluronan hydrogels and rehydrated cross-linked hyaluronan hydrogels contain an organized porous network with pores having an opening with oblong shape, wherein the largest width of the opening is between 125 μm and 460 μm and the smallest width of the opening is between 105 μm and 450 μm.

In certain preferred embodiments of the invention, sterilized cross-linked hyaluronan hydrogels and rehydrated cross-linked hyaluronan hydrogels do not exhibit any tear or rip.

In certain preferred embodiments of the invention, a sterilized cross-linked hyaluronan hydrogel or a rehydrated cross-linked hyaluronan hydrogel retains the shape that it had before being sterilized. In other preferred embodiments of the invention, a sterilized cross-linked hyaluronan hydrogel or a rehydrated cross-linked hyaluronan hydrogel retain the shape that it had been cut into.

In yet another aspect, the present invention provides a kit comprising a sterilized cross-linked hyaluronan hydrogel and a container containing the hydrogel under sterile conditions. In certain embodiments, the kit further comprises a rehydration medium, such as a cell culture medium.

In still another aspect, the present invention provides for the use of a crosslinked hyaluronan hydrogel described herein in an application involving 3D cell culture.

These and other objects, advantages and features of the present invention will become apparent to those of ordinary skill in the art having read the following detailed description of the preferred embodiments.

DEFINITIONS

Throughout the specification, several terms are employed that are defined in the following paragraphs.

As used herein, the term "hydrogel" has its art understood meaning and refers to a water-swellable polymeric matrix that can absorb water to form gels of varying elasticity. The term "matrix" refers to a 3D network of macromolecules held together by covalent and/or non-covalent crosslinks. On placement in an aqueous environment, dry hydrogels swell to the extent allowed by the degree of cross-linking. The amount of water absorbed can be controlled by the macromolecule component used. A hydrogel can enclose or comprise a pharmaceutically active agent and/or a biologically active agent.

The terms "pharmaceutically active agent" and "therapeutically active agent" are used herein interchangeably. They refer to a substance, molecule, compound, agent, factor or composition effective in the treatment of a disease or a condition.

The term "biologically active agent" refers to a substance, molecule, compound, agent, factor or composition that affects (e.g., modifies, prevents, inhibits, reverses, or enhances) a biological event or biological mechanism. Some biologically active agents may be pharmaceutically active agents.

As used herein, the term "effective amount" refers to any amount of a substance, molecule, agent, factor or composition that is sufficient to fulfil its intended purpose(s), e.g., a desired biological or medicinal response to a cell, tissue, system or subject.

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

Other terms are defined in the following section when needed.

DETAILED DESCRIPTION OF CERTAIN PREFERRED EMBODIMENTS

As mentioned above, the present invention provides a method for obtaining a cross-linked hyaluronan hydrogel that is suitable for use in applications involving 3D cell culture. A method according to the invention has the advantage of yielding a hyaluronan hydrogel that allows for a better migration of the cells in the 3D matrix.

I—Methods of Processing a Cross-Linked Hyaluronan Hydrogel

A method according to the invention generally comprises lyophilizing a cross-linked hyaluronan hydrogel and sterilizing the lyophilized hydrogel. The sterilization is performed in two consecutive steps, the first step comprising heating the lyophilized hydrogel and the second step comprising immersing the lyophilized hydrogel in alcohol and submitting the immersed hydrogel to physical compression.

1—Cross-Linked Hyaluronan Hydrogels

Cross-linked hyaluronan hydrogels that can be processed according to a method of the present invention include any cross-linked hyaluronan hydrogel that is suitable for use in applications involving 3D cell culture.

As mentioned above, hyaluronans are glycosaminoglycans (GAGS) consisting of disaccharide units that are themselves composed of D-glucuronic acid and D-N-acetylglucosamine, linked together via alternating β-1,4 and β-1,3 glycosidic bonds. In vivo, polymers of hyaluronan can range in size from $5 \times 10^3$ to $2 \times 10^6$ Da. In certain preferred embodiments, a cross-linked hyaluronan hydrogel is prepared using high molecular weight hyaluronans, for example hyaluronans with a molecular weight of at least $1 \times 10^6$ Da.

Hyaluronans have high turnover rates in vivo and, utilized as such, yield scaffolds that are fragile and unstable, affecting their ability to be used in practical ways needed for in vitro cultures. Therefore, hyaluronan scaffolds suitable for use in a method of the present invention are preferably "stabilized" by chemical (covalent) cross-linking. In a scaffold, the hyaluronan molecules may be cross-linked by any suitable covalent chemical bond. In certain embodiments, the hyaluronan molecules are cross-linked through aldehyde bridges. In other embodiments, the hyaluronans are cross-linked through disulfide bridges.

Cross-linked hyaluronan hydrogels that can be processed according to a method of the present invention may be prepared using any suitable fabrication method. Methods for cross-linking macromolecules and for preparing hydrogels are known in the art. Example 1 provides a description of such a method.

Cross-linked hyaluronan hydrogels suitable for use in a processing method of the invention may consist of, or consist essentially of, cross-linked hyaluronan. Examples of hydrogels consisting essentially of cross-linked hyaluronan include, but are not limited to, the hydrogels described in Prestwich et al., J. Control. Release, 1998, 53: 93-103; Rowley et al., Biomaterials, 1999, 20: 45-53; Comisar et al., Biomaterials, 2007, 28: 4409-4417; Ferreira et al., Biomaterials, 2007, 28: 2706-2717; and Chua et al., Biomaterials, 2008, 29: 1412-1421; and hydrogels commercially available from Lifecore Biomedical LLC, Glycosan Biosystems, and BD Biosciences.

Alternatively, a cross-linked hyaluronan hydrogel may comprise cross-linked hyaluronan and any of a variety of biomolecules, whose presence is desirable in a hydrogel intended to be used as a scaffold for 3D cell culture. Examples of such biomolecules include, but are not limited to, extracellular matrix components such as collagens (such as type I, III, IV or V collagen), basal adhesion molecules (such as laminins or fibronectins), proteoglycans or glycosaminoglycan chains (such as heparin chondroitin sulfate, dermatan, heparin sulfate or proteoglycans thereof), hormones (such as insulin, transferrin, growth hormone, tri-iodothyronine, glucagon, and the like); growth factors (such as epidermal growth factor (EGF), fibroblast growth factor (FGF), transforming growth factor (TGF-β), hepatocyte growth factor (HGF), leukemia inhibitory factor (LIF), interleukin 6 (IL-6), interleukin 11 (IL-11), interleukin 13 (IL-13), interleukin-8 (IL-8), interleukin 3 (IL-3), interleukin 5 (IL-5), granulocyte macrophage stem cell factor (GM-SCF), granulocyte stem cell factor (G-SCF), erythropoietin (EPO), thrombopoïetin (TPO), oncostatin M); chemoattractants (such as peptides integrin motif (RGD), collagen, Kelastin derived motif $(VGVAPG)_3$ and chemokines SDF1-α) and the like.

Alternatively or additionally, a cross-linked hyaluronan hydrogel suitable for use in a method of the present invention further comprises at least one of a variety of biologically active agents, pharmaceutically active agents, and any combinations thereof.

Methods of preparing hydrogels comprising, or coated with, biomolecules, biologically active agents or pharmaceutically active agents are known in the art.

Alternatively, the biomolecules, biologically active agents and/or pharmaceutically active agents may be added to a crosslinked hyaluronan hydrogel after the matrix has been treated using a method of the present invention. For example, a biomolecule, biologically active agent or pharmaceutically active agent may be added to a processed hydrogel by pre-incubating the hydrogel with a cell culture medium comprising such a biomolecule, biologically active agent or pharmaceutically active agent. The pre-incubation is preferably performed following rehydration of the hydrogel but before seeding of the cells.

2—Processing of a Cross-Linked Hyaluronan Hydrogel a—Lyophilization

The first step of a method according to the invention includes lyophilizing a crosslinked hyaluronan hydrogel or providing a lyophilized crosslinked hyaluronan hydrogel. The terms "lyophilizing" and "freeze-drying", and related terms, are used herein interchangeably. They refer to a dehydration process which works by freezing the material to be lyophilized and then reducing the surrounding pressure and adding enough heat to allow the frozen water in the material to sublime directly from the solid phase to the gas phase.

Lyophilization of the crosslinked hyaluronan hydrogel may be performed using any suitable method. In the laboratory, freezing is carried out by placing the material to be lyophilized in a freeze-drying flask and rotating the flask in a bath, called a shell freezer, which is cooled by mechanical refrigeration using dry ice and methanol or liquid nitrogen. On a larger scale, freezing is usually done using a freeze-drying machine. Generally, the freezing temperatures are between −50° C. and −80° C. It is within the knowledge of one skilled in the art to select suitable conditions under which to perform the lyophilization of a hyaluronan hydrogel.

In certain embodiments, the lyophilized crosslinked hyaluronan hydrogel obtained is stored prior to sterilization. Preferably, the lyophilized hydrogel is stored at temperatures below 0° C. For example, after lyophilization, the hydrogel is stored at about −20° C., or at a temperature lower than −20° C. (e.g., about −30° C., about −50° C., about −80° C.).

In certain embodiments, the lyophilized crosslinked hyaluronan hydrogel obtained is cut to a desired shape and desired dimensions prior to sterilization. Generally, the desired shape (geometry) and dimensions (size) will be dictated by the intended use of the hydrogel (e.g., 3D cell culture, tissue engineering, or pharmacological tests). The hydrogel may be cut using any suitable method and means. For example, the hydrogel may be cut manually using a sharp blade. However, in certain embodiments, the hydrogel will preferably be cut using a cutting or slicing machine, e.g., a computer-controlled cutting machine, which allows for better reproducibility in terms of geometry and size. If desired, or if necessary for the application intended, the dimensions of the cut hydrogel obtained may be determined, for example, using a picture processing software such as Saisam®.

In certain embodiments, the crosslinked hyaluronan hydrogel is stored following lyophilization, and is then cut to the desired shape and dimensions prior to sterilization. In other embodiments, the lyophilized hyaluronan hydrogel is cut to the desired shape and dimensions following lyophilization and then stored until it is submitted to the sterilization procedure.

b—Sterilization

In a method of the present invention, the sterilization procedure is performed in two consecutive steps. The first step comprises heating the lyophilized hyaluronan hydrogel and the second step comprises immersing the lyophilized hydrogel in alcohol and submitting the immersed hydrogel to a physical compression.

The first step (i.e., heating) may be performed under any conditions and using any means as long as (1) the resulting hydrogel is sterilized and (2) the conditions and means used for heating the hydrogel do not significantly affect its architecture. Preferably, the hydrogel is submitted to a temperature of about 100° C. for 30 minutes to 1 hour. In certain preferred embodiments, the heating step is carried out by placing a container containing the hydrogel into an oil bath heated at 100° C. One skilled in the art will know how to adapt these conditions and means, which are suitable for use in the laboratory, to a larger scale preparation.

The second step of the sterilization procedure comprises immersing the lyophilized hydrogel in alcohol and submitting the immersed hydrogel to physical compression. In certain preferred embodiments, the hyaluronan hydrogel is immersed in a bath of pure ethanol at room temperature. The immersion results in the hydrogel being in contact with the alcohol.

The terms "physical compression" and "physical pressure" are used herein interchangeably. They refer to an effect which occurs when a force is applied on a surface. Thus, submitting an immersed hydrogel to physical compression means subjecting the hydrogel to a compressive stress or force, resulting in reduction of the hydrogel volume. In the practice of the present invention, the reduction in volume undergone by the hydrogel is mostly temporary and only lasts while the compressive stress is exerted.

The present inventors have found that such a treatment (i.e., compressive stress applied while the hydrogel is immersed) allows the elimination of air bubbles or air pockets that are generally present within lyophilized hydrogels due to the freeze-drying procedure. The presence of these air bubbles or air pockets prevents a good rehydration of the hydrogel to take place. Indeed, the exchange between air, which is rather hydrophobic, and the rehydration medium, which is an aqueous solution, is a slow process. A partial rehydration of a scaffold (due to the presence of remaining air in the hydrogel) results, in turn, in an incomplete invasion or occupation of the scaffold by cells, and therefore in a less than satisfactory 3D cell culture. In fact, the Applicants have demonstrated that hydrogels that were prepared according to a method of the invention with the exception that they were not submitted to compressive stress while immersed in ethanol provided an environment that was less favorable to 3D cell culture than the hydrogels obtained using a method of the invention (see Example 4). Furthermore, they found that while hydrogels of the invention retained their parallelepipedic shape following rehydration and cell culture, hydrogels that were not submitted to compression had a sagging and distorted shape and presented tears or rips.

In the practice of the present invention, submitting an immersed crosslinked hyaluronan hydrogel to physical compression may be performed using any suitable method that results in elimination of the air trapped inside the hydrogel. Preferably, such a method does not significantly and/or permanently alter the architecture of the scaffold. Thus, for example, the hydrogel may be manually pressed against the bottom surface of the alcohol container in which the hydrogel is immersed. In that case, the compressive force may be applied directly on the hydrogel using a finger, or it may be applied to a plane surface (e.g., a glass slide) that is put on top the hydrogel, or it may be applied to one or more than one (e.g., one or two) cylindrical surface (e.g., a glass rod) that are rolled onto the hydrogel. Alternatively, the immersed hydrogel may be placed between two plane surfaces and a compressive force may be applied on one or both surfaces. One skilled in the art will know how to select the materials of the alcohol container and/or of the plane or cylindrical surfaces that enter in contact with the sterilized hydrogel during the physical compression step. Examples of suitable materials include, but are not limited to, glass, ceramic, Teflon, titanium, anodized aluminum, and the like.

The compression pressure to be applied will be sufficient to eliminate any air bubbles or air pockets present inside the immersed hydrogel. Generally, the compression pressure will be in the range of 1 kPa to 1000 kPa. The compression pressure may be kept constant over the whole step of physical compression. However, alternatively, the compression pressure may be increased or decreased over time (either continuously or by increment).

In certain embodiments, between the step of heating the lyophilized hyaluronan hydrogel at 100° C. and the step of immersing the hydrogel into alcohol at room temperature, the hydrogel is left to stand at room temperature under sterile conditions. For example, the hydrogel may be placed in a sterile hood. However, in other embodiments, following the step of heating the lyophilized hyaluronan hydrogel at 100° C., the hydrogel is immediately immersed in alcohol at room temperature.

Following sterilization (i.e., after both the heating and physical compression), and prior to rehydration, the hydrogel may be stored at −20° C. and under sterile conditions.

c—Rehydration

A sterilized crosslinked hyaluronan hydrogel processed according to the present invention is rehydrated prior to use in an application involving 3D cell culture. Rehydration may be performed by any suitable method. Preferably, rehydration is performed by placing the sterilized hydrogel into a rehydration medium at room temperature. The hydrogel is then left to stand in this medium at 37° C. in a 5% $CO_2$ atmosphere until rehydration is complete. In certain embodiments, the hydrogel is rehydrated for several days, for example at least 3 days. The rehydration medium may be any suitable aqueous solution. In certain preferred embodiments, however, the rehydrating medium is a cell culture medium. Preferably, the rehydrating medium used in the rehydration step is the culture medium that is then employed in the 3D cell culture application for which the hydrogel is intended.

Preferably, rehydration is performed for any period of time that is necessary for the rehydration of the hydrogel to be complete (i.e., to reach the equilibrium swelling). The swelling behavior of hydrogels (i.e., increase in mass and volume) that occurs as a result of exposure to a solvent has been studied extensively in the literature. Among other factors, the swelling of a hydrogel is known to depend on the hydrophilicity of the polymer, the nature and degree of the crosslinking, the temperature of rehydration, and the rehydrating medium. One skilled in the art knows that the degree of swelling of a hydrogel can be quantified either by determining the ratio of the volume of the hydrogel in the swollen state to the volume of the hydrogel in the dry state, or by determining the ratio of the weight of the hydrogel in the swollen state to the weight of the hydrogel in the dry state. Therefore, in certain embodiments, rehydration of a hydrogel is performed until the hydrogel is swelled to a desired mass or volume, preferably to a desired mass or volume that corresponds to the swelling equilibrium of the hydrogel.

A rehydrated hydrogel may be used immediately after rehydration, or alternatively, it may be stored at 37° C. in a 5% $CO_2$ atmosphere in a cell culture medium comprising antibiotics to prevent contamination. Under these conditions, the hydrogel may be stored for several weeks. Preferably, the cell culture medium in which the hydrogel is stored is changed at least once a week.

As already mentioned above, prior to cell seeding, the rehydrated hydrogel may be pre-incubated with a cell culture medium comprising at least one of: biomolecules, biologically active agents, pharmaceutically active agents, and combinations thereof.

II—Processed Cross-Linked Hyaluronan Hydrogels

The hydrogels obtained by a method described herein are also encompassed within the scope of the invention.

1—Processed Crosslinked Hyaluronan Hydrogels

A crosslinked hyaluronan hydrogel processed according to a method of the present invention has several properties that are not found in a similar hydrogel which has not been submitted to the same treatment.

In particular, a crosslinked hyaluronan hydrogel processed according to a method of the present invention rehydrates more easily, more completely and more homogeneously than an untreated counterpart. Indeed, as mentioned above, submitting a hydrogel to physical compression results in the elimination of any air that has been trapped inside the hydrogel during a previous freeze-drying procedure. Consequently, a hydrogel according to the present invention presents a degree of swelling that is higher than the degree of swelling of an untreated counterpart. In certain embodiments, the degree of swelling of a hydrogel according to the present invention is at least 1500% higher than the degree of swelling of an untreated counterpart, preferably at least 2000% higher, and more preferably about 2500% higher.

The greater degree of swelling and/or the more homogenous swelling of crosslinked hyaluronan hydrogels processed according to a method of the present invention translate into hydrogels that retain the shape that they were cut into (e.g., parallelepipedic, cubic, and the like) prior to treatment or, if they were not cut into a desired shape, the shape that they had prior to treatment, while hydrogels that were not submitted to compression to remove air bubbles had a sagging and distorted shape (see Example 4).

The greater degree of swelling and/or the more homogeneous swelling of crosslinked hyaluronan hydrogels processed according to a method of the present invention also result in a better migration and more homogeneous occupation of the in the hyaluronan 3D matrix and provide an environment that is more suitable for cell growth and cell colony formation (see Example 4).

Figure 1:
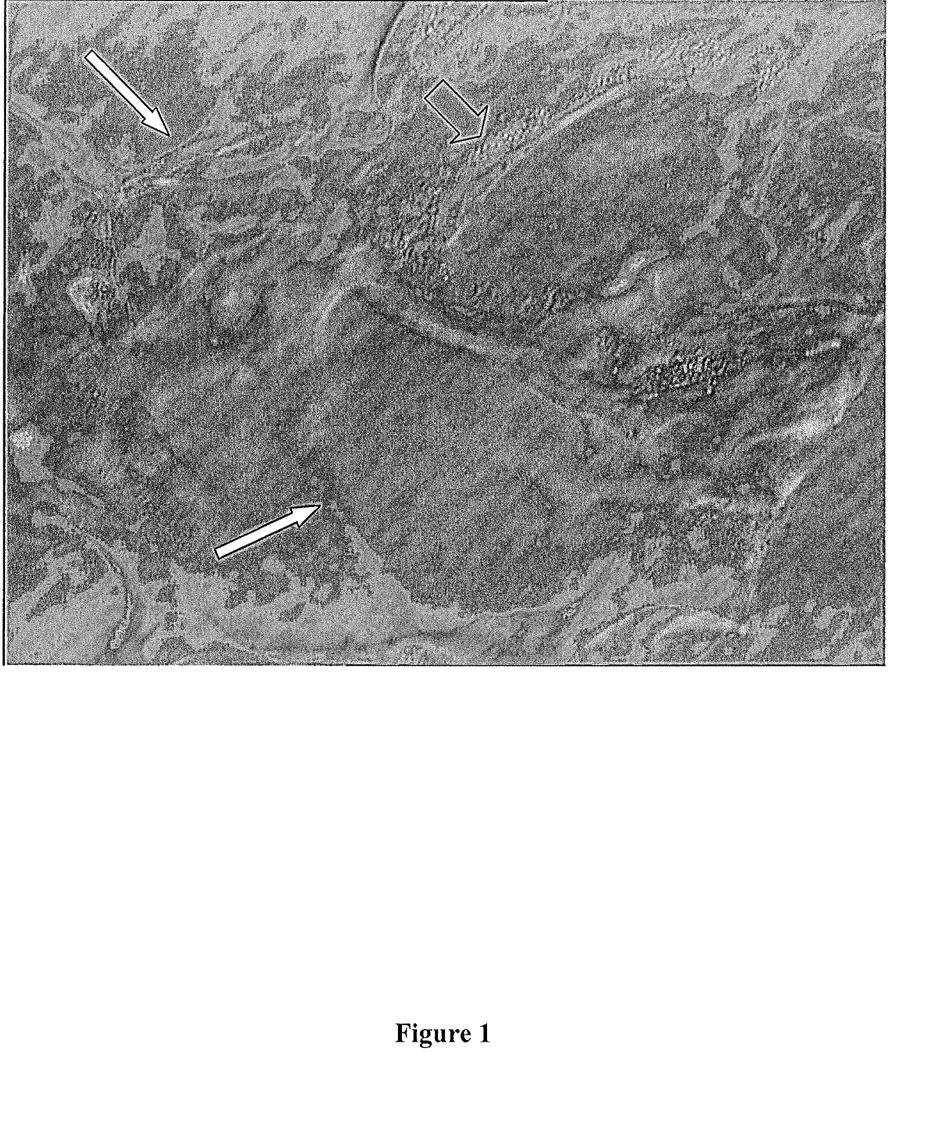
FIG. 1 is a picture of a crosslinked hyaluronan hydrogel containing hematopoietic stem cells one day after incubation (×10). The smaller arrows show interstices of the interconnected porous network and the bigger arrow shows such an interstices when cells have migrated.
Figure 2:
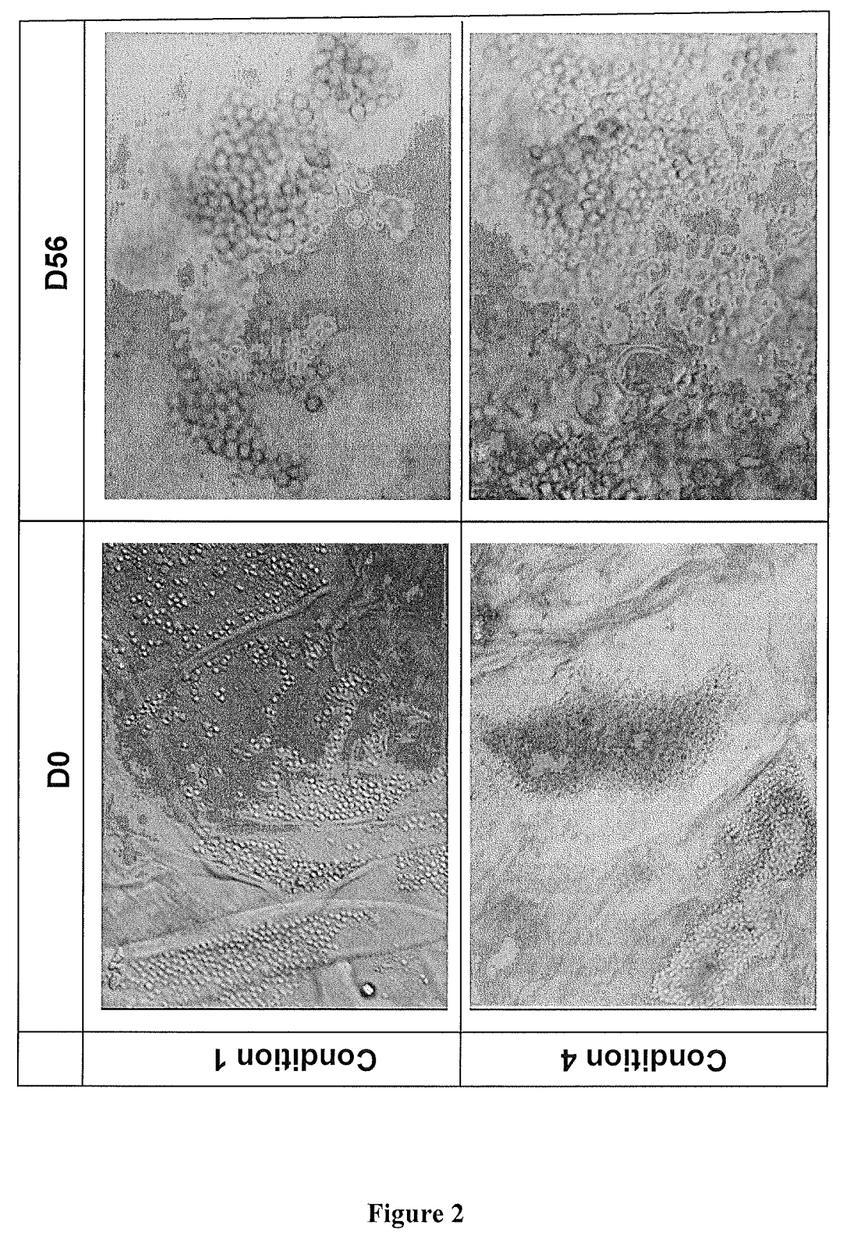
FIG. 2 is a set of four microscope pictures (×100) of colonies of hematopoietic progenitor cells in crosslinked hyaluronan hydrogel at day 0 (D0) and day 56 (D56) under culture condition 1 (50 ng/mL SCF) and culture condition 4 (50 ng/mL SCF, 10 ng/mL VEGF and 300 ng/mL Ang-1).
Figure 3:
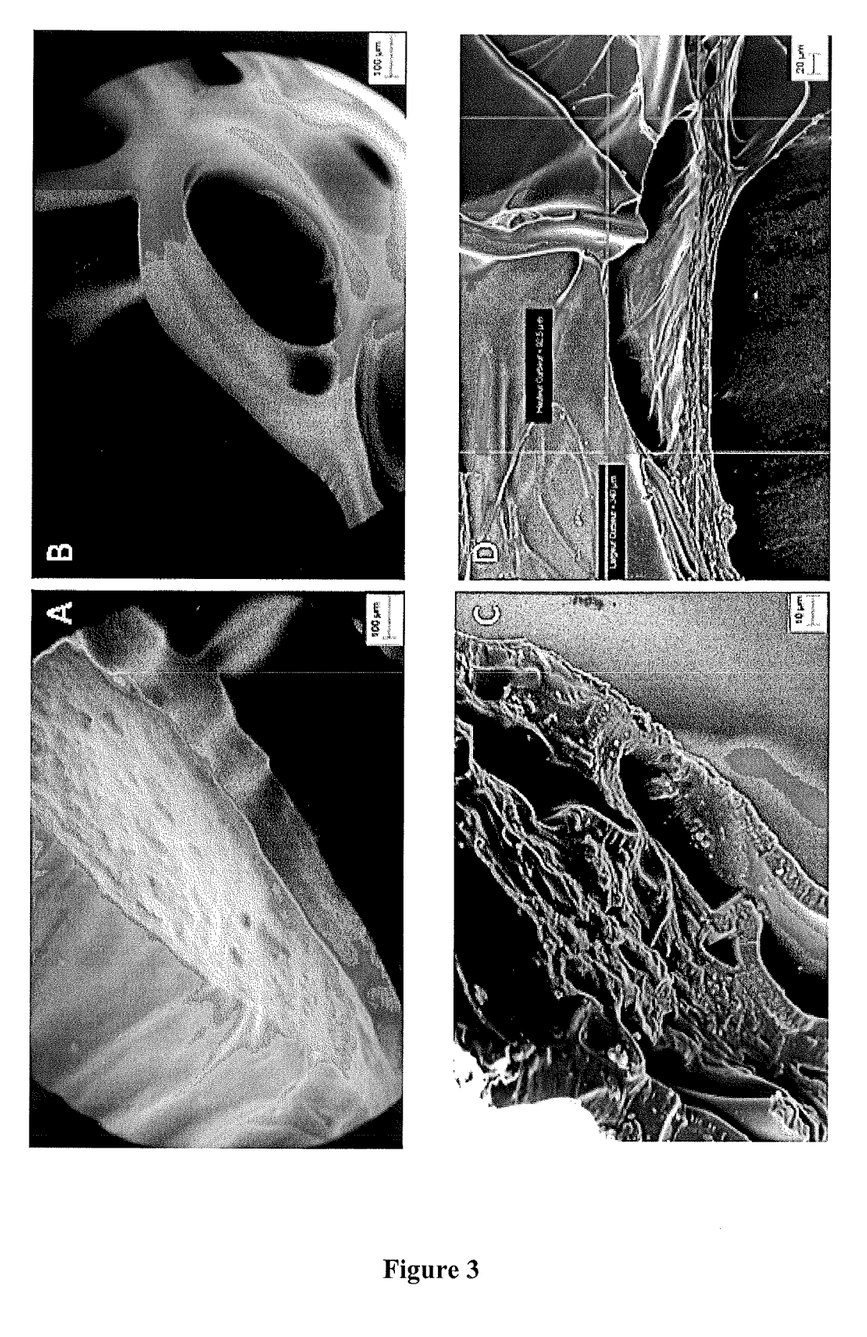
FIG. 3 is a set of Environmental Scanning Electron Microscopy (ESEM) ((A) and (B)) and of Scanning Electron Microscopy (SEM) ((C)) and (D)) cross section micrographs of a hyaluronan hydrogel.

As shown on FIG. 1 and on FIG. 3, a hydrogel of the present invention comprises an interconnected porous network. As used herein, the term "porous network" refers to the combined or total void-volume consisting of the pores and interstices of the hydrogel. The term "pore", as used herein, refers to a cavity or void in the surface, the body or both the surface and body of the hydrogel having at least one outer opening at a surface of the 3D matrix. The term "interstice", as used herein, refers to a cavity or void in the body of the hydrogel not having a direct outer opening at a surface of the 3D matrix. However, an interstice may have an indirect outer opening or pathway to an outer surface of the matrix by way of one or more links or connections to adjacent or neighbor pores and/or interstices. Thus, an interconnected porous network is a porous network comprising pores and interstices, wherein at least some of the interstices have an indirect outer opening or pathway to an outer surface of the 3D matrix.

As shown in the ESEM images of swollen hyaluronan hydrogels obtained by the present inventors (see FIGS. 3(A) and (B)), a hyaluronan hydrogel matrix prepared by a method according to the present invention and cut into a parallelepiped contains a porous network organized in such a way that the parallelepiped presents a smooth upper surface and a smooth lower surface (i.e., upper and lower surfaces without any pore outer openings), and pore outer openings are mainly observed on two parallel faces of the parallelepiped.

In certain preferred embodiments, a hyaluronan hydrogel according to the present invention contains pores that have an outer opening with an oblong or oval shape, wherein the largest width of the opening is between 125 µm and 460 µm and the smallest width of the opening is between 105 µm and 450 µm. Preferably, the mean largest width of the pores is about 235 µm and the mean smallest width of the opening is about 225 µm. It is understood that the outer opening of some pores may have a circular shape.

The greater rehydration properties of a hydrogel of the present invention allow for a more complete and uniform migration and occupation of the cells in the interconnected porous network of the matrix and provide an environment that is more favorable to cell growth and cell colony formation.

2—Sterilized and Rehydrated Crosslinked Hyaluronan Hydrogels

The present invention provides a sterilized crosslinked hyaluronan hydrogel that is obtained, or that is obtainable, using a method of the present invention. Preferably, a sterilized crosslinked hyaluronan hydrogel of the invention is stored under sterile conditions and −20° C. Storage may be performed for very long periods of time (e.g., one year or more).

The present invention also provides a rehydrated crosslinked hyaluronan hydrogel that is obtained by rehydrating a sterilized crosslinked hyaluronan hydrogel of the invention, as described herein. Preferably, a rehydrated crosslinked hyaluronan hydrogel of the invention is stored in a rehydrating medium (e.g., a cell culture medium) at 37° C. and under a 5% $CO_2$ atmosphere. Preferably, the rehydrating medium comprises antibiotics to prevent contamination. Under these conditions, storage may be performed for several weeks as long as new rehydrating medium is added at regular intervals, e.g., every week or every 10 days.

As mentioned above, crosslinked hyaluronan hydrogels of the present invention (whether sterilized or rehydrated) retain the shape that they were cut into (e.g., parallelepipedic, cubic, etc. . . . ) or that they had before treatment. They do not exhibit any, or any significant number of, tears or rips. They contain an organized interconnected porous network with pores having an outer opening with an oblong or oval shape, wherein the largest width of the opening is between 125 µm and 460 µm and the smallest width of the opening is between 105 µm and 450 µm.

III—Uses of Processed Cross-Linked Hyaluronan Hydrogels

As already mentioned above, compared to a similar hydrogel that has not been subjected to a method described herein, a crosslinked hyaluronan hydrogel of the present invention exhibits improved properties. These improved properties result in a higher capability and suitability for 3D cell culture. Therefore, the hydrogels of the present invention may be used in any of a large variety of applications involving 3D cell culture, and in particular in any one of the applications in which hyaluronan hydrogels have been used so far. The term "application involving 3D cell culture", as used herein, refers to any use (of the hydrogel) that includes cell culture in 3 dimensions. In such an application, 3D cell culture may be the ultimate goal or it may only be a step to achieve the ultimate goal.

Cells that can be cultured in 3 dimensions using a hydrogel of the present invention include stem cells, induced pluripotent stem cells, progenitor cells, and differentiated cells. Suitable cells may be of a single cell types (e.g., cardiomyocytes or fibroblasts) or may comprise at least two different cell types (e.g., keratinocyte-fibroblast co-culture). Preferably, cells to be cultured on a crosslinked hyaluronan hydrogel of the present invention are of mammalian (animal or human) origin. Mammalian cells may be of any organ, fluid or tissue origin (e.g., brain, liver, skin, lung, kidney, heart, muscle, bone, bone marrow, blood, amniotic fluid, umbilical cord blood, etc) and of any cell type (see below). Cells may be primary cells, secondary cells or immortalized cells (i.e., established cell lines). They may be isolated or derived from ex vivo biological samples or obtained from volunteers or patients by techniques well known in the art, or alternatively they may be purchased from commercial resources (for example, from the American Type Culture Collection, Manssas, Va.). Alternatively or additionally, cells may be engineered to contain a gene of interest such as a gene expressing a growth factor or a receptor, or to contain a defective gene, or yet to contain Oct3/4, Sox2, Klf4, and c-Myc genes in order to prepare human induced stem cells from adult somatic cells.

Examples of adult differentiated cells that can be grown in a 3D hydrogel matrix of the present invention include, but are not limited to, basal cells, epithelial cells, platelets, lymphocytes, T-cells, B-cells, natural killer cells, reticulocytes, granulocytes, monocytes, mast cells, neurocytes, neuroblasts, glioblastom, cytomegalic cells, dendritic cells, macrophages, blastomeres, endothelial cells, interstitial cells, Kupffer cells, Langerhans cells, littoral cells, tissue cells such as muscle cells and adipose cells, osteoblasts, fibroblasts, and the like.

Examples of progenitor cells that can be grown in a crosslinked hyaluronan hydrogel of the present invention include, but are not limited to, hematopoietic progenitor cells, endothelial progenitor cells, neural progenitor cells, mesenchymal progenitor cells, osteogenic progenitor cells, stromal progenitor cells, and the like. For example, the present inventors have demonstrated the feasibility of 3D culture of hematopoietic progenitor cells in a crosslinked hyaluronan hydrogel (see Examples section).

Examples of stem cells that can be grown in a 3D hydrogel matrix of the present invention include, but are not limited to, embryonic stem cells, adult stem cells and induced pluripotent stem cells.

The cell culture is conducted using "appropriate culture medium and conditions". The term "appropriate culture medium and conditions" refers to a culture medium and to condition that support survival and proliferation of cells cultured in a matrix. Such culture media and conditions are known in the art or may easily be optimized by one skilled in the art.

Examples of applications involving 3D cell culture in which a crosslinked hyaluronan hydrogel of the invention can be used include, but are not limited to, proliferation of cells and tissues in vitro in an environment that more closely approximates that found in vivo (for example as research tools), screening of pharmaceutical compounds and toxicology assays in such cell cultures or tissues in vitro, cell therapy, cell delivery, drug delivery, biochemical replacement, production of biologically active molecules, tissue engineering (e.g., ex vivo organ model, tissue explants, in vivo tissue regeneration), biomaterial, and clinical trials.

IV—Kits

In another aspect, kits are provided that comprise a sterilized crosslinked hyaluronan hydrogel of the invention and a container containing the hydrogel under sterile conditions. Other kits are provided that comprise a rehydrated crosslinked hyaluronan hydrogel of the invention and a container containing the hydrogel in a rehydrating medium comprising antibiotics.

A kit of the invention may further comprise instructions for storing the sterilized hydrogel, and/or instructions for rehydrating the sterilized hydrogel, and/or instructions for storing the rehydrated hydrogel, and/or instructions for using the rehydrated hydrogel. A kit may further comprise one or more of: rehydrating medium and/or reagents; antibiotics; biomolecules, biologically active agents, and/or pharmaceutically active agents as described herein, cell culture medium and/or reagents, cells, seeding means, and the like.

The different additional reagents included in an inventive kit may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers (e.g., vials, ampoules, test tubes, flasks, bottles or assay plates) suitable for conducting certain procedures (e.g., rehydration, cell culture, screening, etc. . . . ) may also be provided. The individual containers of the kit are preferably maintained in close confinement for commercial sale.

Optionally associated with the kit may be a notice or package insert in the form prescribed by a governmental agency regulating the manufacture, use or sale of pharmaceutical or biological products, which notice reflects approval by the agency of manufacture, use or sale for human or animal administration.

An identifier (e.g., a bar code, radio frequency, ID tags, etc. . . . ) may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Synthesis of Crosslinked Hyaluronan Hydrogels

The hyaluronan (HA) hydrogels used were prepared using a long-chain of hyaluronan cross-linked with adipic dihydrazide (ADH, Sigma) as cross-linking agent and 1-ethyl-3-[3-(dimethylamino)-propyl]carbodiimide (EDCI, Sigma) as reagent. All hydrogels were prepared from high molecular weight hyaluronan (>1×10$^6$ Da) according to the procedure described by Prestwich et al. (J. Control. Release, 1998, 53: 93-103). Briefly, the ratios of ADH to hyaluronan and of hyaluronan to EDCI were adjusted to obtain hydrogels optimized for cell adhesion and culture. The best results were obtained with a ratio of ADH to hyaluronan equal to 10:1 and a ratio of hyaluronan to EDCI equal to 1:1. Hyaluronan and hydrazide cross-linker (ADH) were dissolved in milliQ-water and the pH was adjusted to 4 by adding 0.1 N HCl. The carbodiimide reagent (EDCI) was dissolved in milliQ-water and added to the reaction mixture, and allowed to gel for 2 hours with gentle agitation. Hyaluronan hydrogels were equilibrated in 0.1 N NaCl for 2 days, than in a mixture water/ethanol (3/1, v/v) for 2 days, and in milliQ-water for 2 days to remove ADH. Crosslinked hyaluronan hydrogels thus obtained were then treated or processed according to the invention.

Example 2

Processing of Crosslinked Hyaluronan Hydrogels

Crosslinked hyaluronan hydrogels obtained as described in Example 1 were first lyophilized. Each hydrogel was dialyzed, placed in a plastic container and frozen. Following freezing, the hydrogels were placed in a lyophilizer (Alpha 1-2—performances: 2 kg of ice per 24 hours, T=−55° C.). Depending on the volume of water to be eliminated, the lyophilisation was carried out for 4 to 5 days. The lyophilized hydrogels were then stored at −20° C.

Prior to sterilization, the lyophilized hydrogels were cut into rectangular parallelepipeds (about 5×5×1.5 mm). The cut hydrogels were sterilized at 100° C. for 1 hour using an oil bath. The hydrogels were then immersed in pure ethanol and manually compressed to eliminate air trapped within the hydrogel structure. The hydrogels were then rehydrated using a cell culture medium (e.g., RPMI (Eurobio) comprising antibiotics) until they swelled a 100-fold in volume.

Example 3

Characterization of Processed Crosslinked Hyaluronan Hydrogels

An inverted microscope picture of a crosslinked hyaluronan hydrogel treated according to a method of the present invention and seeded with hematopoietic stem cells is presented on FIG. 1. The picture was taken 24 hours after seeding. This figure clearly shows the porous structure of the hydrogel as well as the presence of cells in some of the interstices.

Scanning Electron Microscopy (SEM) and Environmental Scanning Electron Microscopy (ESEM) were used to characterize the hyaluronan hydrogels and their interactions with cells. Scaffolds were incubated in glutaraldehyde (1% PBS) for 1 hour at 4° C. Then, the samples were snap dessicated for 2 hours at 40° C. The samples were then coated with an argon layer and examined using SEM EVO®40 series (Carl Zeiss AG, Germany). Since the ESEM technique does not require dehydration of the samples, the surface of hydrated scaffolds was directly observed by the same SEM equipment with a Peltier-cooled cold plate with a surface temperature of 0° C. (Carl Zeiss AG, Germany). The scaffold pore sizes were determined by measuring pores from ESEM images. The ESEM and SEM images of hyaluronan hydrogels are presented on FIG. 3(A)-(D).

ESEM was also used to analyze the fine structure of hyaluronan hydrogels after cell culture (at day 56). The interactions between cells and hyaluronan hydrogels were analyzed by SEM.

Isolation of CD34$^+$ CBCs.

Cold blood samples were collected with the informed consent of the children's parents in agreement with French ethical laws. Mononuclear cells (MNCs) were isolated by gradient density separation (d=1.077, Percoll, Sigma, France). The cells obtained were washed twice in Hank's medium (Eurobio, France), and then depletion of monocytes was performed by plastic adherence during 45 minutes (37° C.; 5% $CO_2$) in RPMI 1640 containing 10% of fetal calf serum (FCS).

The CD34$^+$ MNC fraction was isolated by microbeads selection using a Vario magnetic affinity cell sorting (MACS) separator and MS separation columns (Miltenyi Biotec, France). This isolation was performed by positive selection of CD34$^+$-expressing cells. The CD34$^+$ cells were suspended in phosphate-buffered solution (PBS, Eurobio, France), 0.1% bovine serum albumin (BSA, Sigma-Aldrich, France), and 2 mM EDTA buffer (Sigma-Aldrich, France). They were directly labeled by incubation for 30 minutes at 4° C. with a monoclonal antibody coupled to microbeads. The cells were washed in a separation buffer and laid on an MS column placed in a magnetic field. The magnetically labeled CD34$^+$ cells were retained on the column, after removal of the column from the magnetic field, cells can be eluted as the positively selected fraction, while unlabelled CD34$^-$ cells pass through.

The purity of CD34$^+$ cells was evaluated by FACS with anti-CD34 monoclonal antibody conjugated to fluorescein isothiocyanate (clone 581, Beckmann Coulter, France). The purity of cord blood CD34$^+$ cells was between 93%-95%.

Hyaluronan Hydrogel Culture of CD34$^+$ CBCs.

Prior to cell seeding, hyaluronan hydrogels were incubated for 24 hours in RPMI1640 complemented with human SDF-1α at 100 ng/mL (R&D System, France) then washed with PBS, in order to facilitate cell migration and colonization into the hydrogels.

In each well, 5×10$^4$ CD34$^+$ CBCs were cultured in 2 mL of Stemspan (StemCell Technologies, UK) with 50 ng/mL of SCF (R&D System, France) and 0.1% of Penicillin and Streptomycin. Three hyaluronan hydrogels prepared as described above, were placed in each culture well (except in liquid control). Cultures were incubated (37° C.; 5% $CO_2$) for 1, 28 or 56 days. Each week, one half of the culture liquid phase was replaced with fresh medium. After centrifugation, cells were restituted in their own culture well.

Morphology of Adherent Cells on Hyaluronan Hydrogel.

SEM imaging at day 56 was used to monitor the interaction of CD34$^+$ CBCs on hyaluronan hydrogel. Hematopoietic cells were intimately attached to the matrix (FIG. 4).

Figure 4:
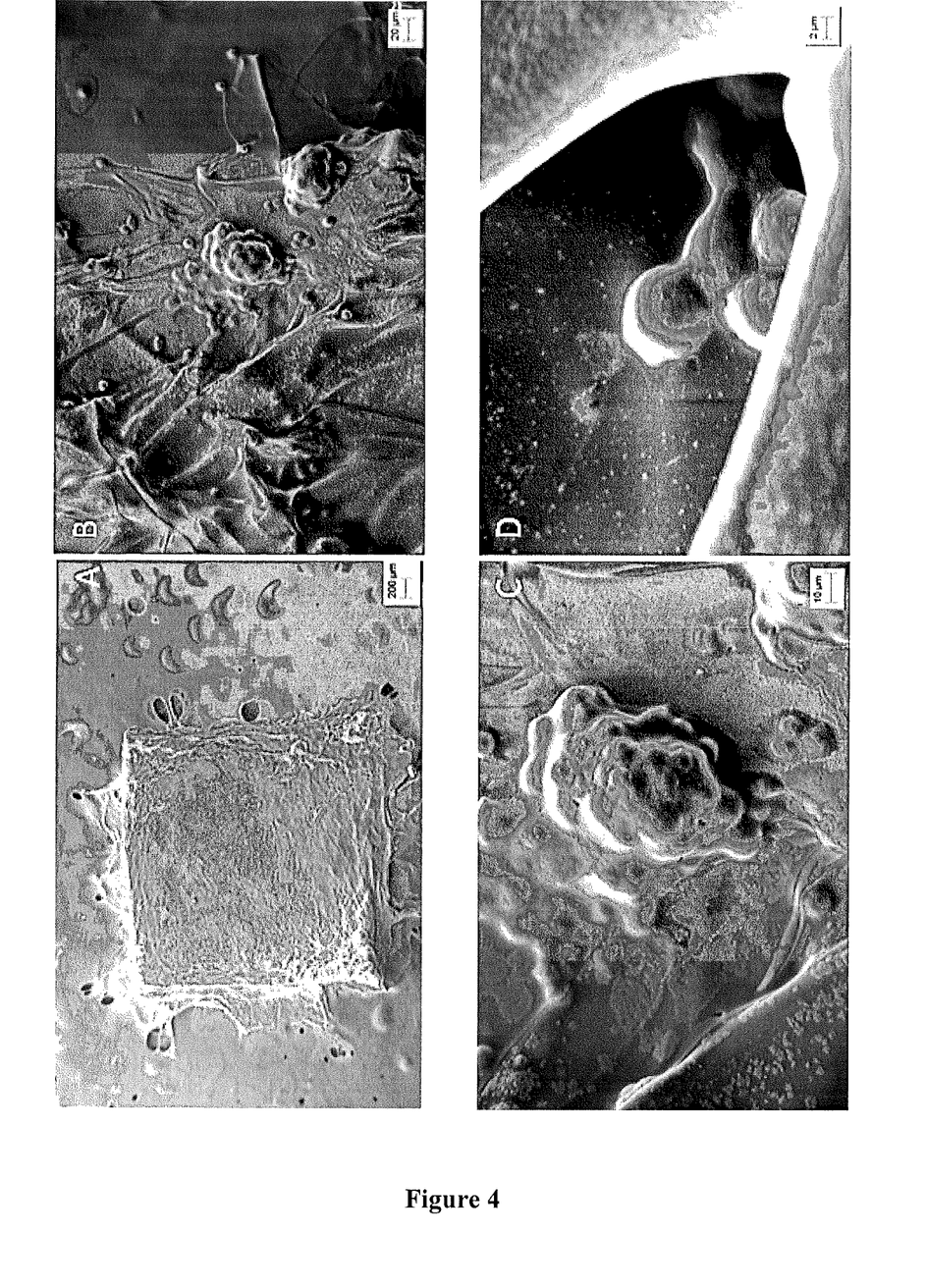
FIG. 4 is a set of SEM micrographs of $CD34^+$ CBCs on a hyaluronan hydrogel after 56 days of culture.

The distinct non circular cell colonies most likely arose from single or small clusters of cells proliferating in a radial manner on the scaffold (FIGS. 4(A) and (B)). The adherent cells were anchored to the matrix via numerous uropodia radiating from the cell surface (FIGS. 4(C) and (D)).

Example 4

Effects of the Method of Preparation of Crosslinked Hyaluronan Hydrogels

Two different methods were used for preparing crosslinked hyaluronan hydrogels and the effects of the preparation methods on the hydrogels' properties were analyzed. The first method was the same as that described in Examples 1 and 2 (i.e., a method according to the present invention). The second method was identical except that after being sterilized at 100° C., the hydrogels were immersed in pure ethanol and then directly rehydrated using a cell culture medium. In other words, in the second method, the hydrogels were not manually compressed to eliminate air trapped within the hydrogel structure. Prior to cell seeding, both sets of hydrogels (i.e., compressed and non-compressed) were then incubated for 24 hours in RPMI1640 complemented with human SDF-1α at 100 ng/mL (R&D System, France) then washed with PBS, in order to facilitate cell migration and colonization into the hydrogels. Then, the hydrogels were seeded with $CD34^+$ CBCs as described in Example 3.

SEM images of both sets of hydrogels at day 35 after seeding were recorded in order to compare the properties of the hydrogels obtained using the two different preparation methods. Some of the SEM images obtained are presented on FIG. 5.

Figure 5:
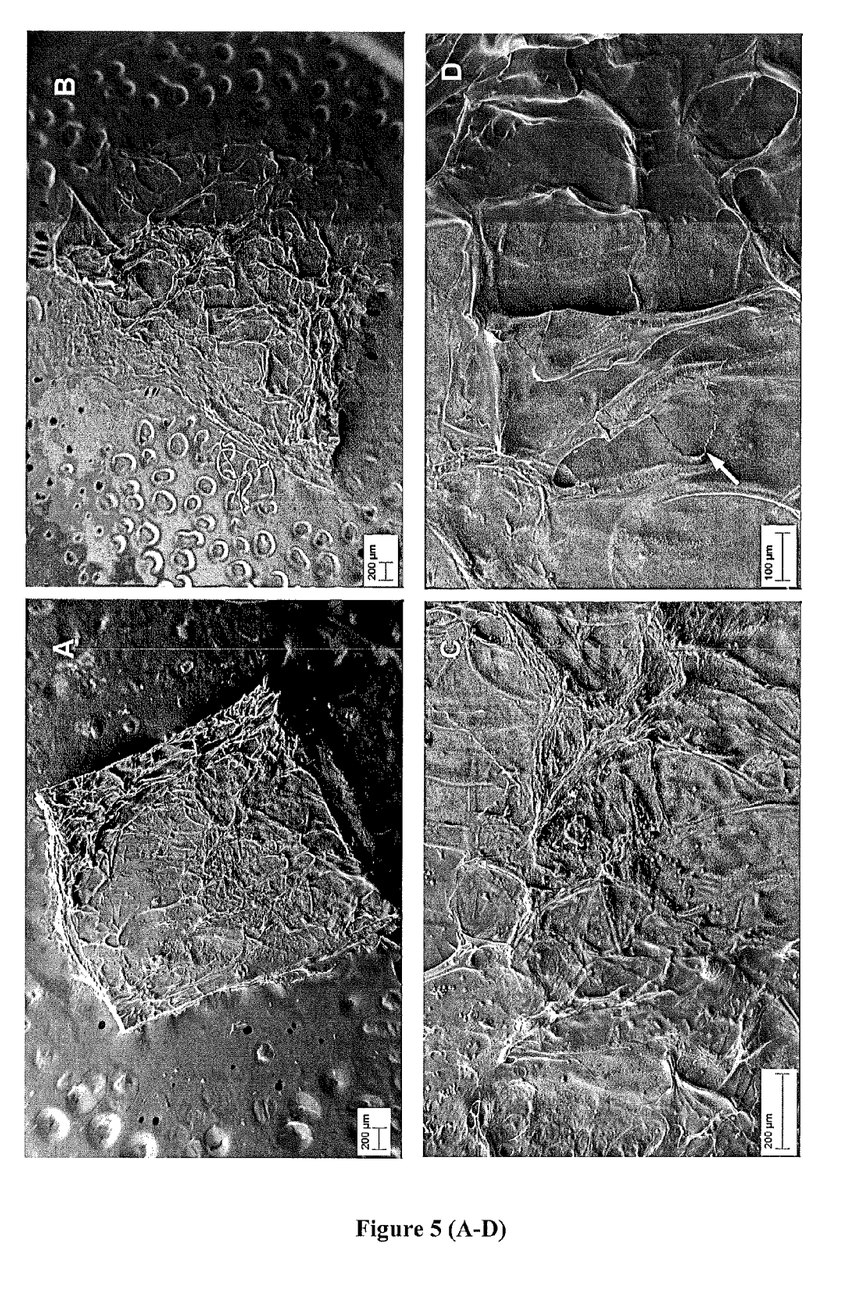
FIG. 5 is a set of SEM micrographs of $CD34^+$ CBCs on hyaluronan hydrogels after 35 days of culture. In (A), (C), (E) and (G), the hyaluronan hydrogels were prepared according to a method of the present invention. In (B), (D), (F) and (H), the hyaluronan hydrogels were prepared according to a method of the present invention except that they were not submitted to physical compression. In (D), the arrow shows the presence of a tear in the hydrogel. In (E), the arrow shows a cell colony, while in (F), the arrows show single cells.

As seen on FIG. 5(A), even after rehydration and cell culture, the hydrogels prepared according to the present invention retained their parallelepipedic shape, while the hydrogels that had not been submitted to immersion in ethanol and physical compression had a distorted and sagging shape (see FIG. 5(B)). Furthermore, tears of the scaffold were only observed in the case of the hydrogels that were not submitted to compression (see FIG. 5(D)).

In addition, cell migration was more complete, uniform, and organized in hydrogels that were prepared according to the method of the invention than in hydrogels that were not submitted to compression (see, for example, FIG. 5(C) where cells can be observed over the entire picture, while in FIG. 5(D) or (F) only a small number of sparsely scattered cells are observed). Furthermore, groups of cells or cell colonies were commonly found in hydrogels prepared according to the method of the invention (see, for example, FIGS. 5(C) and (E)) while they were extremely rare in hydrogels that were not submitted to compression (see, for example, FIGS. 5(D) and (H)), suggesting that an improved culture environment is provided in the former case.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:
1. A method for obtaining a cross-linked hyaluronan hydrogel suitable for 3D cell culture, wherein the cross-linked hyaluronan hydrogel contains an organized, interconnected porous network with pores having an outer opening with an oblong or oval shape, is free of any tear or rip; and retains its shape following rehydration, said method comprising steps of:
  (a) lyophilizing the cross-linked hyaluronan hydrogel to obtain a lyophilized hyaluronan hydrogel or providing a lyophilized hyaluronan hydrogel; and
  (b) sterilizing the lyophilized hyaluronan hydrogel
    first by heating the hydrogel, and
    then by immersing the hydrogel in absolute ethanol at room temperature and subjecting the hydrogel to physical compression while the hydrogel is immersed in absolute ethanol, wherein the step of subjecting the hydrogel to physical compression eliminates any air trapped in the hydrogel.

2. The method according to claim 1, wherein the heating is performed for 1 hour using an oil bath at 100° C.

3. The method according to claim 1 further comprising a step of:
  prior to sterilization, cutting the lyophilized hyaluronan hydrogel to desired shape and dimensions.

4. The method according to claim 1 further comprising a step of:
  following sterilization, storing the sterilized hyaluronan hydrogel under sterile conditions at −20° C.

5. The method according to claim 1 further comprising, following step (b), a step of:
  rehydrating the sterilized hydrogel, until the sterilized hydrogel reaches a swelling equilibrium.

6. The method according to claim 5 further comprising a step of:
  following rehydration, storing the rehydrated hyaluronan hydrogel rehydrating medium comprising antibiotics, at 37° C. and in a 5% $CO_2$ atmosphere.

* * * * *